(12) United States Patent
Beil et al.

(10) Patent No.: US 10,184,875 B2
(45) Date of Patent: Jan. 22, 2019

(54) APPARATUS AND METHOD FOR DETERMINING THE PARTICLE SIZE AND/OR THE PARTICLE SHAPE OF PARTICLES IN A PARTICLE STREAM

(71) Applicant: Retsch Technology GmbH, Haan (DE)

(72) Inventors: Sebastian Beil, Geilenkirchen (DE); Stephan Knop, Hagen (DE)

(73) Assignee: RETSCH TECHNOLOGY GMBH, Haan (DE)

( * ) Notice: Subject to any disclaimer, the term of this patent is extended or adjusted under 35 U.S.C. 154(b) by 0 days.

(21) Appl. No.: 15/518,456

(22) PCT Filed: Oct. 15, 2015

(86) PCT No.: PCT/EP2015/002046
§ 371 (c)(1),
(2) Date: Apr. 11, 2017

(87) PCT Pub. No.: WO2016/058699
PCT Pub. Date: Apr. 21, 2016

(65) Prior Publication Data
US 2017/0315039 A1    Nov. 2, 2017

(30) Foreign Application Priority Data

Oct. 15, 2014  (DE) .................. 10 2014 015 056
Nov. 28, 2014  (DE) .................. 10 2014 017 552

(51) Int. Cl.
*G01N 15/02*       (2006.01)
*G01N 15/14*       (2006.01)
*G06M 1/10*        (2006.01)

(52) U.S. Cl.
CPC ..... *G01N 15/0227* (2013.01); *G01N 15/0211* (2013.01); *G01N 15/147* (2013.01);
(Continued)

(58) Field of Classification Search
CPC ............... G01N 15/0227; G01N 15/02; G01N 15/0211; G01N 15/1456; G01N 15/1429; G01N 15/147; G01M 1/101
See application file for complete search history.

(56) References Cited

U.S. PATENT DOCUMENTS 5,786,894 A * 7/1998 Shields .................... G01N 1/38
                                                         250/574
6,061,130 A    5/2000 Plate et al.
(Continued)

FOREIGN PATENT DOCUMENTS

DE         19802141 C1    4/1999
DE      10200902077 A1    1/2010
(Continued)

OTHER PUBLICATIONS

International Search Report for corresponding International Application No. PCT/EP2015/002046, dated Feb. 26, 2016.
(Continued)

*Primary Examiner* — Sang H Nguyen
(74) *Attorney, Agent, or Firm* — Jason H. Vick; Sheridan Ross, PC

(57) ABSTRACT

A device (1) is described and represented for the determination of the particle size and/or the particle shape and/or optical properties, such as transparency, of particles (2) in a particle stream (3), with a feeding device (4) for the feeding of the particles (2) to a measuring zone (5), wherein the particles (2) flow through the measuring zone (5), with at least one illuminating device (6) for illuminating the measuring zone (5), with at least two camera devices (7, 8), each of which photographs a measurement region (9, 10) of the measuring zone (5) associated with the corresponding camera device (7, 8), wherein a first camera device (7) photographs a first, preferably larger, measurement region (10) with a first, preferably lesser, magnification and a second (Continued)

Figure 3:
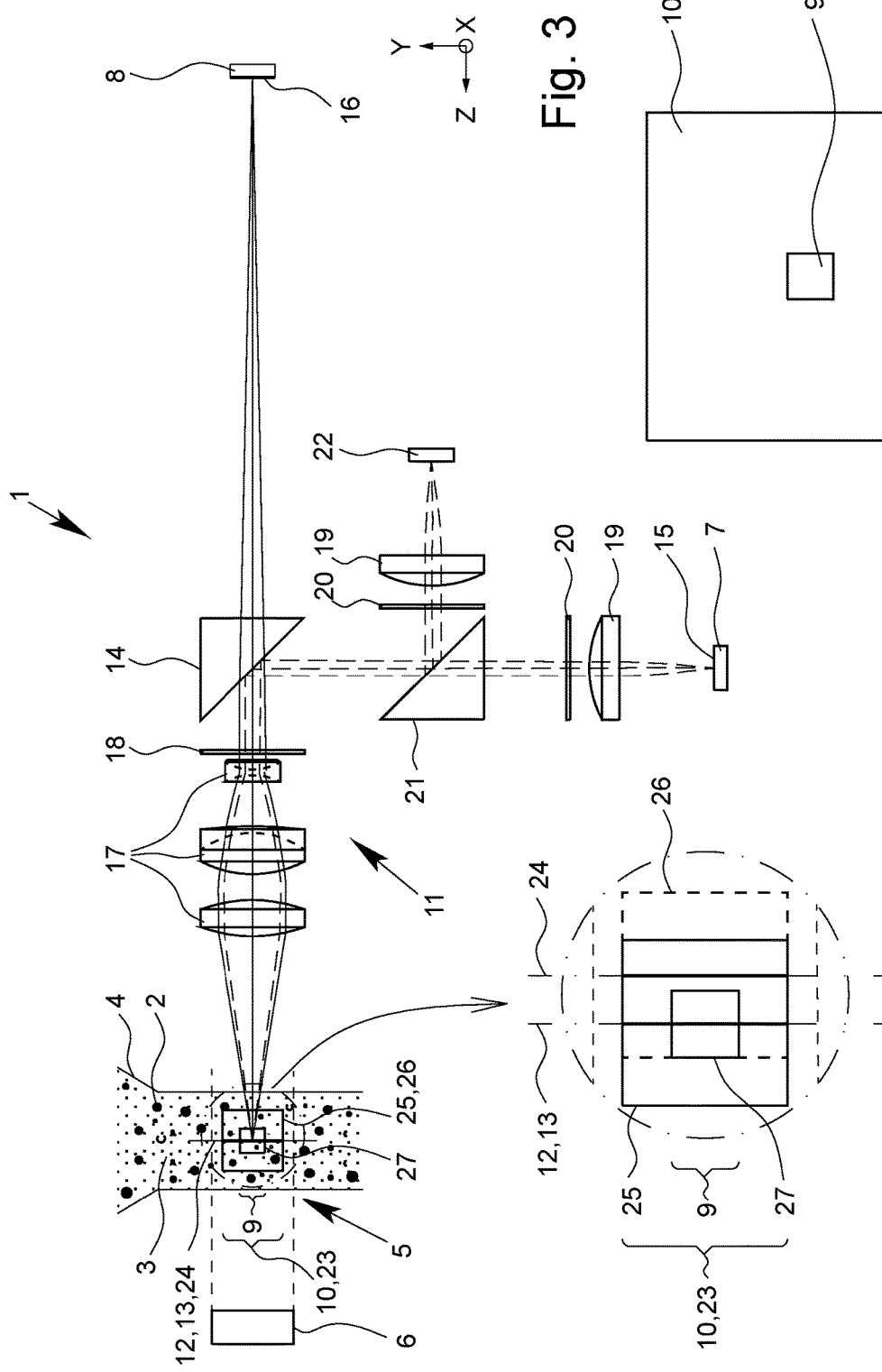

camera device (8) photographs a second, preferably smaller, measurement region (9) with a second, preferably stronger, magnification, with an imaging optics (11) for imaging the measurement regions (9, 10), and with an evaluating device for determining the particle size and/or the particle shape from the photographs of the measurement regions (9, 10), wherein the imaging optics (11) comprises at least one optical element (14), at which and/or by which the light radiation emanating from the measuring zone (5) is divided into at least two beam portions. According to the invention, it is provided that the illuminating device (6) is designed such that the first measurement region (10) and the second measurement region (9) are always illuminated together, wherein the first measurement region (10) is illuminated with the same intensity as the second measurement region (9).

15 Claims, 7 Drawing Sheets

(52) U.S. Cl.
CPC ..... *G01N 15/1429* (2013.01); *G01N 15/1456* (2013.01); *G06M 1/101* (2013.01); *G01N 2015/144* (2013.01); *G01N 2015/1497* (2013.01)

(56) References Cited

U.S. PATENT DOCUMENTS

| | | | | |
|---|---|---|---|---|
| 6,133,995 | A * | 10/2000 | Kubota | G01N 15/1459 356/337 |
| 9,448,161 | B2 * | 9/2016 | Ostermeyer | G01N 21/59 |
| 2007/0013910 | A1 * | 1/2007 | Jiang | G01N 15/0205 356/336 |
| 2007/0222987 | A1 * | 9/2007 | Palumbo | G01N 15/0227 356/338 |
| 2008/0231854 | A1 | 9/2008 | Seifert et al. | |
| 2014/0009621 | A1 | 1/2014 | Tucker et al. | |
| 2014/0234865 | A1 * | 8/2014 | Gabriel | G01N 15/1459 435/7.21 |
| 2015/0369722 | A1 * | 12/2015 | Donner | G01N 15/1459 73/864.72 |
| 2016/0202164 | A1 * | 7/2016 | Trainer | G01N 15/0211 356/336 |

FOREIGN PATENT DOCUMENTS

EP 1972921 A1 9/2008
WO WO 99/15877 4/1999

OTHER PUBLICATIONS

Written Opinion for corresponding International Application No. PCT/EP2015/002046, dated Feb. 26, 2016.

* cited by examiner

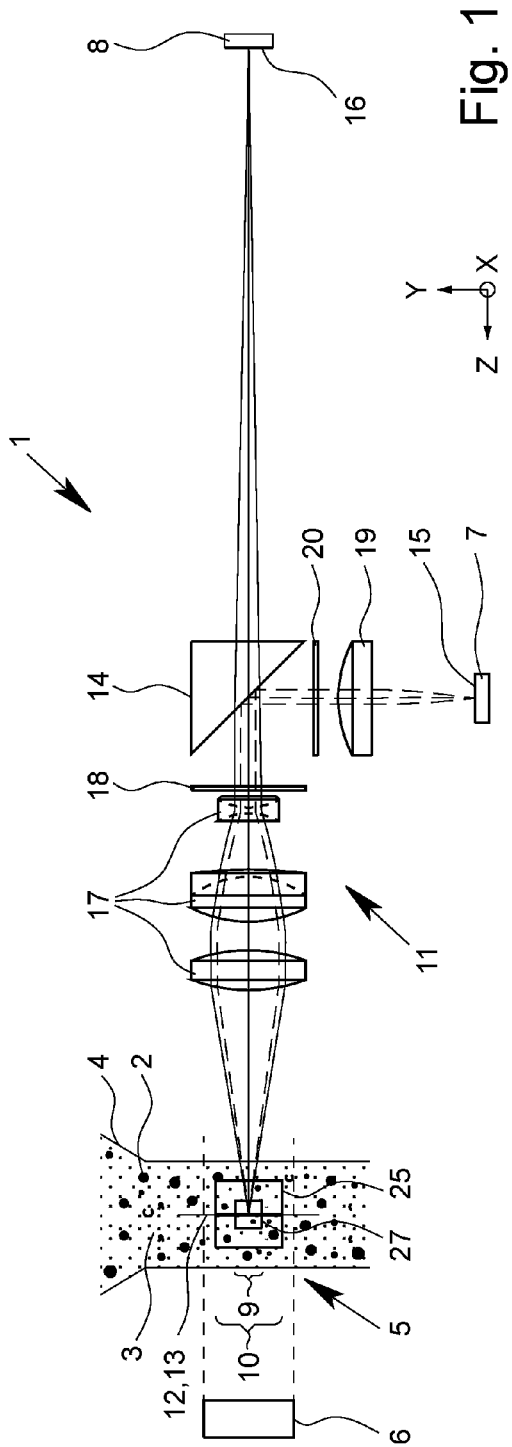
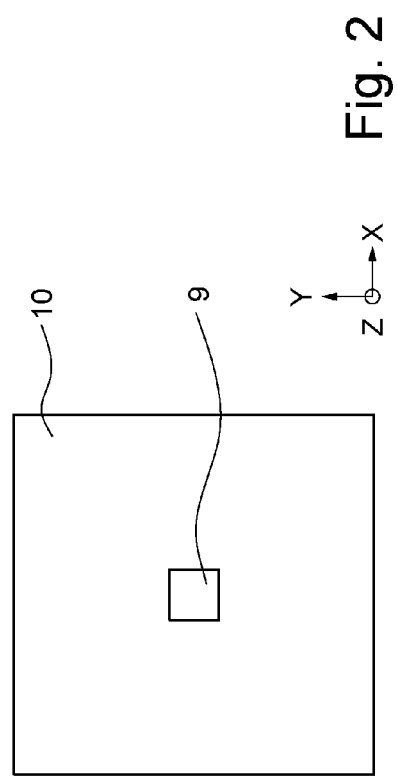

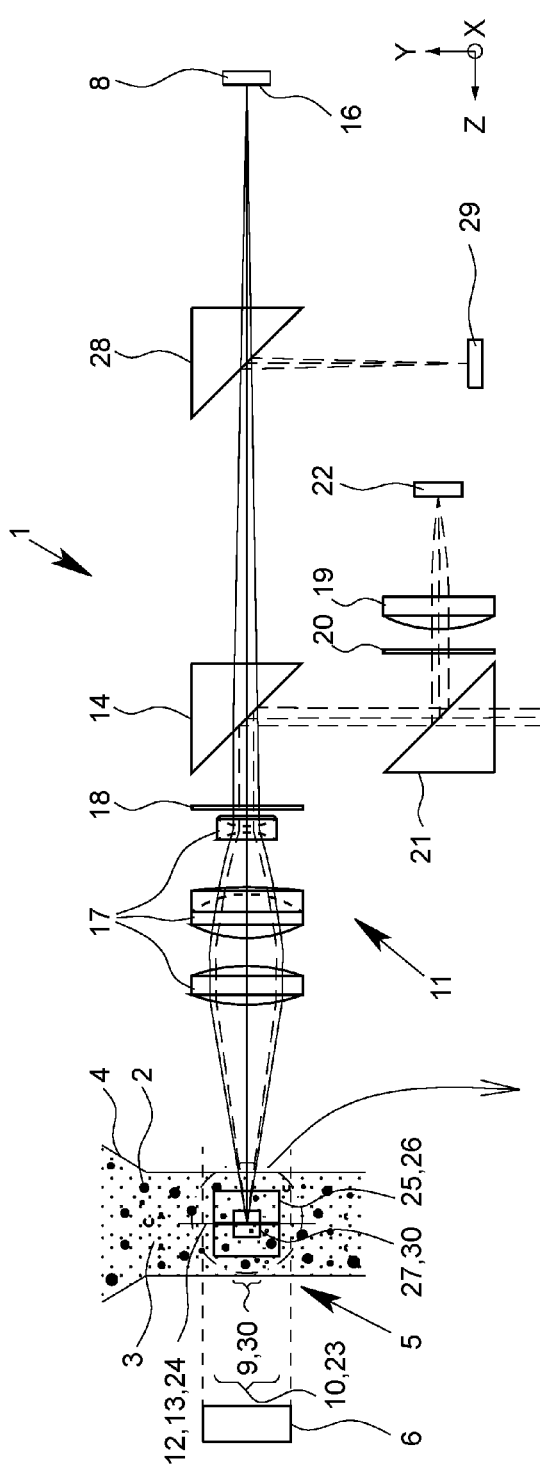
Fig. 5
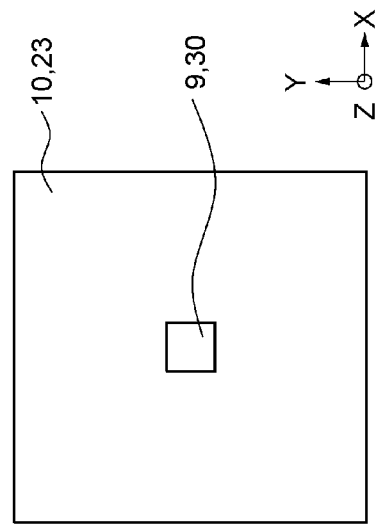
Fig. 6
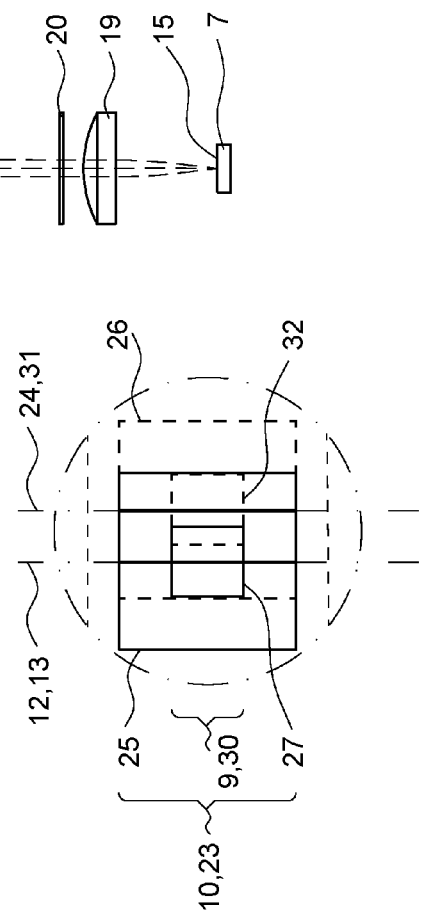

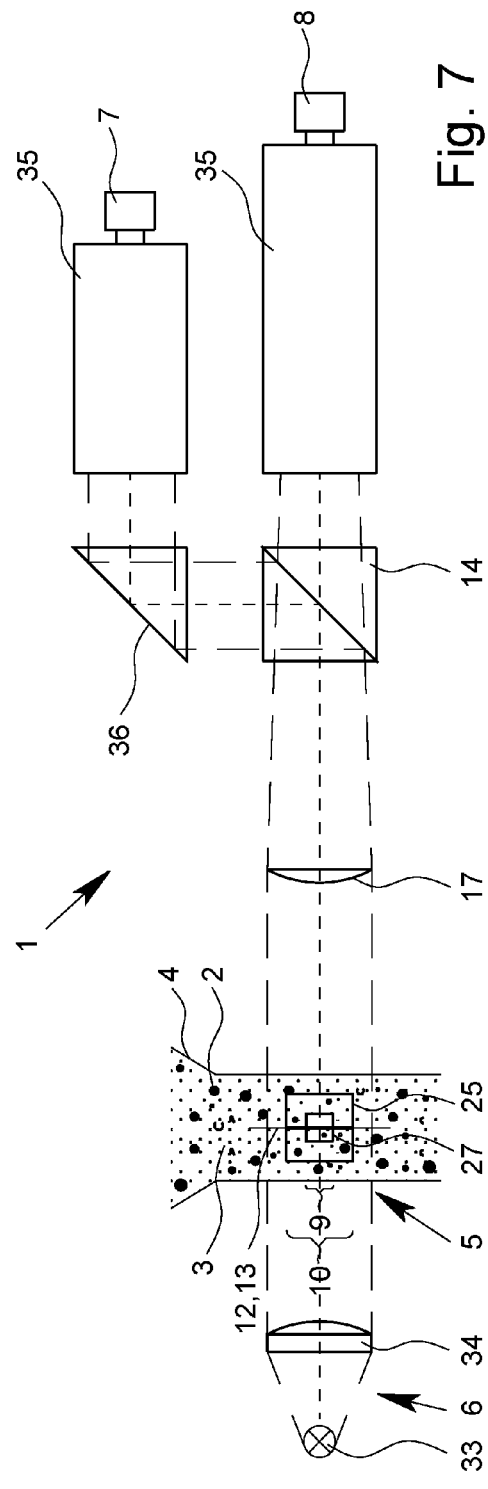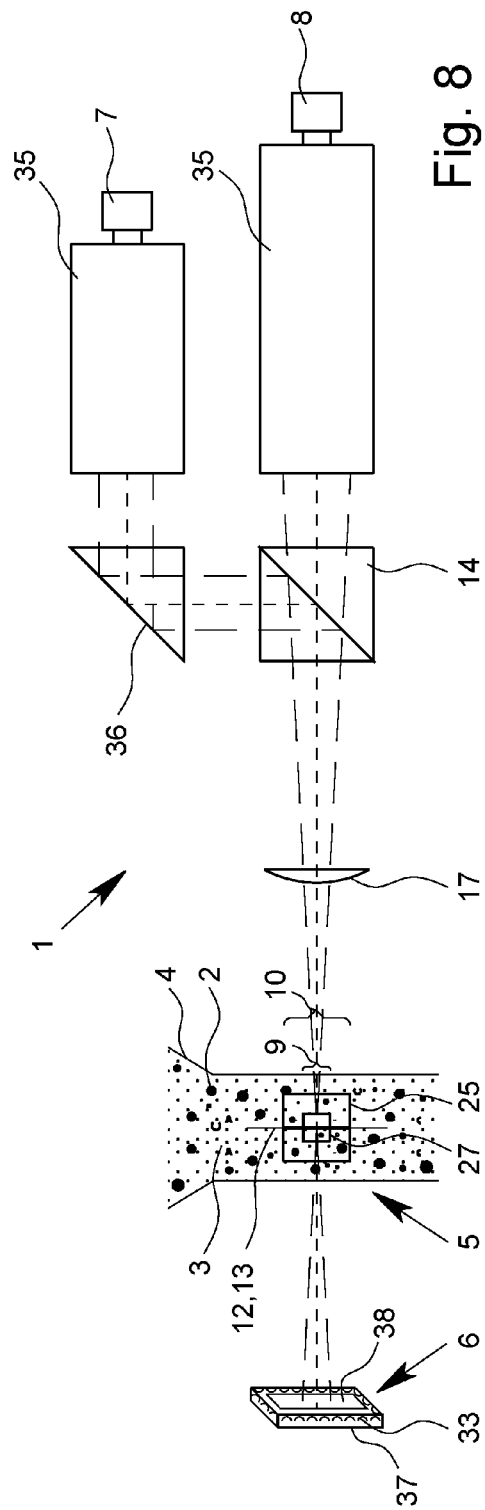

APPARATUS AND METHOD FOR DETERMINING THE PARTICLE SIZE AND/OR THE PARTICLE SHAPE OF PARTICLES IN A PARTICLE STREAM

CROSS REFERENCE TO RELATED APPLICATIONS

This application is a national stage application under 35 U.S.C. 371 of PCT Application No. PCT/EP2015/002046 having an international filing date of 15 Oct. 2015which designated the United States, which PCT application claimed the benefit of German Application No. 10 2014 015 056.9 filed 15 Oct. 2014 and German Application No. 10 2014 017 552.9 filed 28 Nov. 2014, each of which are incorporated herein by reference in their entirety.

The invention concerns a device with the features of the preamble of claim 1. Furthermore, the invention concerns a method with the features of the preamble of claim 15.

Devices of the aforementioned kind serve to characterize particles of a particle mixture in terms of their size and/or their shape. A typical area of use of such devices is for example quality control during the production or use of particle-shaped materials. It is generally the case that the particles of the particle mixture are at first separated by a feeding device and supplied to a measuring zone, through which the particles pass in the form of a particle stream. In the region of the measuring zone, the particles are illuminated by a suitable illuminating device and electro-optically detected by a detection device, such as a digital matrix camera. The illumination is preferably stroboscopic, and the light sources used are preferably light-emitting diodes or semiconductor lasers. Usually the particles coming from the feeding device are accelerated by gratify and move through the detection region between light source and photographing apparatus. In this way, a shadow projection of the particles is created in the photographing apparatus. Shape and size parameters are then determined and calculated from the recorded images of the shadow projections by means of an evaluating unit.

In order to detect the broadest possible spectrum of particle sizes, the largest possible dynamic measurement region is desirable. By this is meant the quotient of the upper and lower measurement limits, that is, the maximally and minimally detectable particle size. From DE 198 02 141 C1 there is known a device which accomplishes this goal by the use of two or more matrix cameras with different imaging scales. A further reduction of the lower measurement limit is accomplished by a device described in EP 1 972 921 A1. The device described there comprises two light sources, which illuminate as optimally as possible the two measuring zones. The measuring zones are recorded with two different magnifications, with the smaller measuring zone recorded with higher magnification being illuminated much more strongly than the larger measuring zone recorded with lesser magnification. Thus, the two pairs of light sources and photographing units produce two independent beam paths. The two beam paths are arranged so that the smaller measuring zone is located at the center of the larger measuring zone. In combination with the external dimensions of the objectives used, a cross geometry is produced for the two beam paths. As a result of the crossing beam paths, the viewing fields of the cameras and thus the object planes of the corresponding images are tilted relative to each other. From the circumstance that the particle stream thus does not run parallel to the two camera image sensors or object planes, a limitation results on the measurement volume of the two measurement regions of the measuring zone. The measurement volume here is the volume in which a particle evaluation is possible by the imaging on the image plane, that is, the image sensor of the camera. The limitation of the measurement volume can in some cases influence the detection probability for small particles and thus the evaluation statistics.

Furthermore, an arrangement with crossing beam paths is a disadvantage when using additional glass surfaces, such as in the form of a flow cell, in the region of the measuring zone, since a spatial offset of beams occurs when beams do not impinge perpendicularly on the interface boundary of two materials with different index of refraction. Ultimately this can lead to an optical distortion of the image recorded.

In order to ascertain the actual shape and size parameters of the particles of the particle stream from the images recorded, it is necessary to first calibrate the camera image with a calibration standard. In the case of crossing beams, this results in a considerable adjustment expense, since a calibration standard for each beam has to be introduced with high precision into the measuring zone perpendicular to the corresponding beam.

EP 1 972 921 A1 discloses another embodiment of a particle measuring device, in which the directions of illumination and the directions of recording each coincide in the region of the measuring zone thanks to the use of semitransparent mirrors. It is also provided here to illuminate with different intensities two regions of the measuring zone which are recorded with different magnifications.

However, problems may occur with the image presentation and image evaluation when using the particle measuring devices known from EP 1 972 921 A1 if two measurement regions that are partly overlapping and recorded with different magnification are illuminated at different intensities. This problem occurs especially in the investigation of transparent or semitransparent particles. A perturbation of the image recorded can occur especially in the viewing field of the camera with lesser magnification. Partial regions of the image are overexposed in this case, so that there are many pixels which are too bright or even saturated. As a result, particle edges can no longer be identified clearly and particles can no longer be recognized clearly. Both of these factors have a negative impact on the accuracy of the particle measurement. Moreover, when investigating particles of photosensitive material, a stronger illumination in one of the measurement regions can cause in particular chemical changes in the particles and/or chemical reactions of the particles in this measurement region, such as do not occur in the less intensely illuminated measurement region. This also can lead to a falsified measurement result in the particle investigation. It is also suspected that diffraction effects occur, which may be detrimental to the measurement precision.

The problem which the present invention proposes to solve is to provide a device and a method for the determination of the particle size and/or the particle shape of particles in a particle stream of the kind mentioned above, in which a large dynamic measurement region is assured with high precision of determination of the particle size and/or the particle shape while at the same time having low adjustment expense, wherein the above described problems of image presentation and image evaluation do not occur or are diminished. Furthermore, the device should be characterized by a very compact design with small structural size.

According to the invention, the aforementioned problem is solved by a device with the features of claim 1 and by a method with the features of claim 15. According to the invention, the illuminating device is designed such that the first measurement region and the second measurement region are always illuminated together, wherein the first measurement region is illuminated with the same intensity as the second measurement region. The measurement regions are located in at least one object plane. The object plane is projected by the imaging optics into at least two preferably nonparallel image planes. However, two parallel image planes are not excluded. In the image planes there are situated the image sensors of the camera devices. Of course, between the measuring zone and the optical element on the one hand and the optical element and the particular camera device on the other hand there can be provided optical devices of the imaging optics, especially lenses. The imaging optics can comprise in particular optical devices which are associated with the camera devices, such as built-in objectives. The described layout of the device of the invention enables the determination of the particle size and/or shape with high precision in a highly dynamic measurement region.

Thanks to a joint, especially homogeneous, illumination of the two measurement regions with the same intensity, the above-described problems in image presentation and image evaluation, especially those caused by scattered light, are diminished or even totally prevented. According to the invention, it is ensured that no relevant local changes in the intensity distribution occur over the surface of the measurement regions.

The optical element or the optical mechanism of the device according to the invention preferably comprises at least one beam splitter. A beam splitter generally comprises a boundary surface on which a certain portion of the impinging light is reflected, while the remaining portion of the light rays pass through the boundary surface. A semi-transparent or partly transparent mirror represents a simple form of a beam splitter.

One form of a beam splitter is for example an arrangement of two prisms, which are cemented together at their base by a bonding agent, such as a resin, thus producing the approximate shape of a cuboid. Such a beam splitter functions by the principle of impeded total reflection. The thickness of the bonding layer and/or the resin material determines the ratio by which the incident light intensity is divided.

In one preferred embodiment of the device according to the invention, the optical element divides the incident light radiation coming from the measuring zone into at least two beam portions, which are identical in spectrum to the incident light radiation. The spectral intensity distribution of the beam portions after the optical element is in this case equal both with respect to each other and with respect to the incident light radiation before the optical element, so that the spectral information of the incident light is not changed by passing through the optical element. Only the overall intensity of each of the beam portions is less than the overall intensity of the incident light radiation.

Of course, there is not only a dividing into beam portions with the same intensity, but a dividing in any given ratio is possible, i.e., into beam portions with different intensity.

Besides the pure intensity division by the optical element, it is conceivable to separate the images from each other depending on wavelength, or to apportion the light radiation coming from the measuring zone into at least two beam portions depending on wavelength. For this, the illuminating device can comprise at least two different-colored light sources for a spectral division of the images. "Different-colored" means in this context that the light sources emit light radiation of different wavelength or in substantially at least two wavelength regions separated from each other. The wavelength separation of the emission maxima of the respective wavelength regions in order to have a good separation of the images is preferably at least 50 nm, more preferably at least 100 nm, especially preferably at least 150 nm. For the separation of the images, a dichroic optical element can be used, especially a dichroic prism, which transmits light of at least one wavelength region and preferably totally reflects light of at least one other wavelength region. An adapting of the illumination intensity of the measurement regions can thus be accomplished first of all by the selection of the wavelength taking into account the spectral sensitivity of the image sensors of the camera device. Furthermore, narrow-band filters, such as interference filters, with a defined optical density can be used for this purpose.

Another possibility for separation of the images is the use of polarized light. This requires that the illuminating device comprise at least one light source which emits light with a defined polarization. An adapting of the light intensity impinging on the different image planes can then be accomplished by the use of at least one polarization filter or at least one polarization filter in combination with at least one wavelength retardation plate, especially a $\lambda/2$ plate. It is conceivable in this context to provide as the optical element for the beam splitting for example a polarizing beam splitter, in which the division ratio is determined by the polarization angle of the incident light, insofar as this is linearly polarized.

It is furthermore possible to accomplish a dividing of the intensity by means of other optical elements. For example, a pinhole mirror can let through the interior portion of a widened beam through an opening in the mirror surface, while the outer annular region of the beam cross section is reflected at an adjustable angle. The division ratio of the intensities substantially depends on the diameter of the opening In order to ensure an illumination of the measuring zone with light in defined wavelength regions, the light sources of the illuminating device used are preferably light-emitting diodes (LEDs) and/or semiconductor lasers. Besides an emission of light in an extremely narrow wavelength range, the latter are additionally distinguished by the emission of polarized light.

The illuminating device is preferably designed for the joint homogeneous illumination of the two measurement regions. A homogeneous illumination of the measurement regions increases the comparability of the measurement results for particles that were measured in different sectors of the measurement region, and at the same time it further lessens the probability of occurrence of the above-mentioned scattered light problems.

For the homogeneous lighting of the measuring zone or the two measurement regions, the illuminating device can have preferably at least one diffuser element, especially a diffuser lens or a scattering disk, between one light source or several light sources of the illuminating device and the measuring zone, so that an area light source is produced.

Alternatively, a homogeneous illumination of the measurement regions can be achieved if a portion of the light radiation given off by a substantially pointlike light source is made parallel, especially by means of a collimator lens or a collimation arrangement.

In the case of several light sources, it is of course also possible to use together, for example, an area light source and a point light with parallelized beam path.

Insofar as particles are to be evaluated comparatively which occur both in the camera image of the one measurement region and in the camera image of the other measurement region, a simultaneous exposure and photographing is required for a clear matching of particles, so that the particles are located at exactly the same spatial position in the measurement region. Due to the high velocity of the particles in the measurement region, this requires a synchronization on a nanosecond time scale, which can only be assured with considerable equipment development using several light sources. This synchronization problem does not occur when using one light source.

In one preferred embodiment of the device according to the invention, the two measurement regions are exposed in sequence, especially in alternation, with light radiation of differing intensity. In this way, always with joint illumination of both measurement regions, and both measurement regions being exposed each time with the same intensity, it is possible to achieve an illumination of the measurement regions with an intensity which is adapted to the magnification at which the corresponding camera device photographs the measurement region.

Preferably, the illuminating device is designed for pulsed illumination of the two measurement regions. The duration and/or the intensity of at least two pulses may be different. Preferably, two pulses of higher and lower intensity or longer and shorter duration alternate over time. A first pulse with lower intensity and/or shorter duration for example can illuminate the two measurement regions, while the first camera device photographs the first, preferably larger, measurement region with a first, preferably lesser, magnification, and a second pulse with higher intensity and/or longer duration can illuminate the two measurement regions while the second camera device photographs the second, preferably smaller, measurement region with a second, preferably greater, magnification.

Thus, for the investigation of the particles, the pictures of the first camera device that were exposed by the first pulse with lesser intensity and/or shorter duration and the pictures of the second camera device that were exposed with the second pulse of higher intensity and/or longer duration are evaluated. The exposure strength is accordingly converted from the spatial to the temporal domain. This ensures that the pictures of each of the camera devices are exposed in suitable fashion, i.e., adapted to the respective magnification of the imaging optics, while the measurement regions at each moment of illumination are illuminated with identical intensity in order to counter the above-mentioned scattered light problems.

In the case of a different pulse length, the emission intensity of the pulses can in particular be identical. Since the exposure time per picture for the camera devices typically used is significantly larger than the usual pulse length for a stroboscopic illumination, a larger amount of light impinges on the camera chip during the integration time of the camera device, so that a picture is taken with a brightness that is sufficient for a satisfactory evaluation.

In order to allow the camera pictures to be matched up with the corresponding illumination pulses or at least make this process easier, preferably at least one camera device is synchronized with the illuminating device.

The measurement regions can be situated in a common object plane or in two different object planes. Preferably, the invention calls for a split-view optics, in which the light beams exiting from the measuring zone or the measurement regions travel to the optical element of the imaging optics for a section of their path parallel with an optical axis. The measurement regions are then located in two parallel object planes or, preferably, in one common object plane, while the principal movement direction of the particle flow in the measuring zone runs parallel to the object planes or the common object plane. This reduces the adjustment expense during the calibration of the device according to the invention. According to the invention, it is not necessary to arrange the two camera devices alongside each other for this, as described in DE 198 02 141 C1, which results in a very compact layout of the device according to the invention.

After the splitting of the beams at and/or by the optical element, at least two different imaging scales can be achieved by the choice of suitable lens systems for the photographed measurement regions. When using digital matrix cameras, at least two different-sized measurement regions are produced for the same size of the image sensors in at least two different imaging scales. Preferably, a second measurement region being photographed with a greater magnification lies within a first measurement region which is photographed with a lesser magnification. More preferably, the second measurement region lies in the middle of the first measurement region. The second measurement region is preferably a subset of the first measurement region.

The imaging focal depth range extending on either side of an object plane along the optical axis, in which an adequate imaging focus is created for the determination of the particle size and/or the particle shape, together with the respective measurement region, produces a measurement volume. Thanks to the choice of suitable lens systems and/or by a shifting of the respective camera device and if necessary the lens system placed in front of it relative to the measuring zone along the optical axis, it is possible to adjust the spacing of the object planes from each other so that the measurement volume of the more magnified measurement region lies entirely in the measurement volume of the less magnified measurement region. This ensures a more dynamic measurement region with higher accuracy in the determination of the particle size and/or particle shape. In particular, it is advantageous for the object planes to lie in a common plane, while the corresponding measurement volumes are intersected centrally. In this way, the accuracy of the determination can be further improved.

The optical element can be designed so that the resulting beam portions have different light intensities. In particular, it is possible in this way for the second measurement region photographed by the second camera device, preferably the smaller measurement region photographed with greater magnification, to be illuminated with a higher intensity than the first measurement region photographed by a first camera device, preferably the larger measurement region photographed with lesser magnification. In this way, each measurement region is illuminated with a sufficiently high intensity or quantity of light. The ratio of the intensity distribution between the two beam portions can be chosen such that the most equal possible magnification settings or gain values can be used for all camera devices.

In an alternative embodiment of the device according to the invention, at least one additional optical element for dividing a beam portion generated at the first optical element into two further beam portions and at least one further camera device are provided. In this case, at least three measurement regions are photographed with three camera devices, with the measurement regions being arranged in three object planes. The object planes in turn can be arranged parallel to each other or they can coincide. Preferably, it is possible to photograph two measurement regions with an identical magnification.

Two measurement regions can be arranged in object planes which are spaced apart from each other in the direction of the optical axis. In this way, it is possible for the measurement volumes of the two measurement regions to pass into one another, so that a broader continuous region results with adequate image sharpness for the evaluation.

Alternatively, however, it is also possible for the measurement volumes of the two measurement regions to coincide.

Of course, additional measurement volumes along the optical axis can be photographed in identical manner by more than two optical elements and a corresponding number of additional camera devices, resulting in a correspondingly larger extent of the detectable volume along the optical axis. The probability that a particle is moving through the detectable region and can thus be detected is correspondingly increased in this way. This is especially significant in the case of a smaller measurement region imaged with greater magnification.

The imaging optics can comprise at least two optical elements, wherein one optical element divides light radiation into at least two beam portions with identical spectrum or identical color and/or identical polarization and another optical element divides light radiation into at least two beam portions with different spectra or colors and/or different polarizations. At the first optical element, for example, a division of the light radiation into two beam portions can occur, which enables a photographing of two measurement regions with different magnification and, preferably, at different illumination intensity. One of the two beam portions is further divided at the second optical element into another two beam portions with different spectra or colors and/or different polarizations. This allows access to spectral or chromatic information at the same time as the spatial imaging.

By selecting camera devices with different detection properties, in particular ones that have a different sensitivity in accordance with the wavelength of the incident light, it is possible for example to have access to spectral or chromatic information at the same time as the spatial imaging.

The imaging optics furthermore can comprise a lens with a variable focal distance. The focal distance of the lens can be electrically variable, in particular. This enables a changing of the imaging properties of the imaging optics in ongoing operation, especially without optical components, especially lenses, needing to be switched out by manual intervention in the assembly.

Alternatively or additionally, the imaging optics can also have a layout corresponding to that of a telescope. This can be of advantage when there are special requirements with respect to the nature of the imaging.

In order to improve the optical imaging properties of the imaging optics, at least one achromatic doublet can be provided in order to reduce the occurrence of chromatic aberrations. To prevent spherical aberrations, the imaging optics can comprise at least one aspherical lens.

Furthermore, the imaging optics can preferably have telecentric imaging properties. At least two independent aperture diaphragms can serve to adjust field depth ranges and thus adjust the measurement volumes associated with the measurement regions.

The present invention also concerns a device for the determination of the particle size and/or the particle shape of particles in a particle stream, with a feeding device for the feeding of the particles to a measuring zone, wherein the particles flow through the measuring zone, with an illuminating device for illuminating the measuring zone, with at least two camera devices, each of them photographing a measurement region associated with the corresponding camera device or an associated image detection surface of the measuring zone, wherein one camera device photographs a first, preferably smaller-area, measurement region with a stronger magnification and another camera device photographs another, preferably larger-area, measurement region with a lesser magnification, and with an evaluating device for determination of the particle sizes and/or the particle shapes by means of the photographs of the measurement regions. Furthermore, the present invention concerns a method for the determination of the particle size and/or the particle shape of particles in a particle stream, wherein particles are fed to a measuring zone and flow through the measuring zone, wherein the measuring zone is photographed with at least two camera devices, wherein one camera device photographs a first, preferably smaller, measurement region with a stronger magnification and another camera device photographs another, preferably larger, measurement region with a lesser magnification, and wherein the particle size and/or the particle shape is determined with the aid of the photographs of the camera devices.

If particle distributions with a different size or with a different size range are to be investigated with the device known from EP 1 972 921 A1, it is necessary to adapt the imaging scale of a camera device to the particle sizes of the grain distribution being investigated. This involves manual activities, such as changing objectives, regulating the depth of focus, changing the camera position and adjusting the device. Furthermore, it is necessary to change accordingly the preset level of the illumination intensity of the measurement region which needs to be photographed with a different magnification, in order to enable photographs with good sharpness and good contrast and prevent an overexposure of the image sensors of the camera device due to overly high illumination intensity. But the setting of an intensity each time adapted to a new magnification of the measurement region involves a time- and labor-intensive adapting of the focusing optics of the illumination system, followed by a readjusting of the device.

Furthermore, in the known device, an adequate illumination of the measurement region being photographed with a stronger magnification requires a high focusing of the laser radiation used for the illumination of this measurement region. The focus is chosen so that the focal diameter amounts to only a few millimeters, which makes it hard to adjust the associated camera device. If the adjustment is not exact, there might result a nonhomogeneous lighting of the measurement region, which is detrimental to the exact determination of the particle sizes and/or particle shapes.

Another problem which the present invention proposes to solve is the providing of a device and a method of the kind mentioned above which enable an easier, especially customer-specific, changing of the imaging scale when photographing a measurement region or even both measurement regions for adapting the imaging scale to a changed size and/or size distribution of the particles in the grain distribution as compared to the known devices and methods. Furthermore, the expense for the adjustment of the device, especially the adjustment of the camera devices, should be reduced and a very homogeneous lighting of the measurement regions should be assured, especially that of the more strongly magnified measurement region.

In order to solve the aforementioned problems, in a device of the kind mentioned above it is provided according to the invention that the illuminating device comprises two light sources, wherein at least a first light source illuminates a first illumination field of the measuring zone and at least a second light source illuminates a second illumination field of the measuring zone, wherein the more magnified measurement region lies in the first illumination field and the less magnified measurement region lies in the second illumination field and wherein the illumination of the two illumination fields and thus of the two measurement regions is done with matching intensities.

The illumination intensity or the lighting strength is the radiant power per unit of area in Watts per square meter and pertains to the total power of the incoming electromagnetic energy impinging on an illumination field or a measurement region, related to the size of the area of the illumination field or the measurement region. It is assumed that the lighting is done with the least possible change in intensity over the area.

"Matching" intensities in the sense of the invention occur in particular when the two illumination fields are illuminated with identical intensity. However, one does not depart from the invention if the illumination of the two illumination fields is done with slightly differing intensities, where the intensity deviation can be less than 5%, especially less than 2%.

The illumination of the two illumination fields and thus of the two measurement regions with matching intensity enables a simple adapting of the magnification of one measurement region or both measurement regions to a particular particle size by adjusting the objective and/or changing the objective, i.e., by a magnification or a reduction of the imaging scale of at least one camera device, without this requiring a changing of the optical system of the illuminating device, made up of light sources and lens systems. In particular, the invention enables an adapting accordingly to the particle size of the magnification of the measurement region being photographed with higher magnification or the imaging scale of the associated camera device. In the context of an adequate image sharpness and an adequate contrast of the photographs, as well as any unwanted overexposure of the image sensors of the camera device, the allowable change in the magnification of one measurement region or both measurement regions for the same unchanged intensity of the lighting is determined by the present level of the illumination intensity which can be achieved with the optical system of the illuminating device and by the light sensitivity of the sensors of the camera devices. As a result, in the invention we do not set an optimal intensity for the particular magnification for every illumination range, as is the case with the device known from EP 1 972 921 A1. In the device known from EP 1 972 921 A1, the ratio of the intensity of a more heavily illuminated region to the intensity of a less heavily illuminated region can in fact amount to 70:1 or more. Instead, according to the invention, a certain equal level of illumination intensity is set for both illumination fields.

It is advisable for the level of the illumination which is set in the device according to the invention and with which the two illumination fields are illuminated to be adapted to a certain predetermined magnification of a (more magnified) measurement region, such as 4×, 8×, 10× or even 12× to 20× magnification. Preferably, the level of the illumination intensity is set so that at least one measurement region at maximum magnification of the measurement region can be photographed with a camera device used in the device without any blurring in the photograph making difficult or even preventing the determination of the particle size and/or the particle shape with the desired precision. For the certain predetermined magnification, the illumination intensity is then optimally set when the size of the region cast in shadow by a particle on the camera sensor corresponds substantially to the actual size of a particle in the photograph, taking into account the imaging scale. In particular, the set intensity should be high enough to ensure good image sharpness with sharp particle edges and a contrast-rich presentation of the particle in the photograph at the given magnification. The set intensity should preferably be such that thirty or more pictures per second can be taken with an exposure time of around 100 to 200 ns or less. In this way, even with particle stream velocities of up to 50 m/s, the desired determination of particle size(s) and/or particle shape(s) can be performed.

Due to the (high) illumination intensity which is set and which is used to irradiate the two illumination fields, the device according to the invention enables in particular a boosting of the magnification of at least one measurement region, especially the (larger) measurement region which is photographed with less magnification, without having to perform a readjustment or adapting of the illumination intensity for this. However, depending on the level of the set illumination intensity, the magnification of the (smaller) measurement region which is photographed with greater magnification can also be increased.

If the illumination intensity is too low on account of the enhancing of the imaging scale, a so-called low-light camera can be used, having more light-sensitive sensors (or a higher ISO sensitivity). The same holds if the level of the illumination intensity which is set in the device according to the invention and which is used to illuminate the two illumination fields is adapted to a comparatively low magnification of a measurement region, such as a 2× or 4× magnification.

On the other hand, the illumination intensity which is set also preferably makes it possible to reduce the imaging scale in the photographing of at least one measurement region, especially the (smaller) measurement region which is photographed under higher magnification, without having to perform a readjustment or adapting of the illumination intensity for this.

Thanks to the use of intensity compensation means, such as diaphragms or filters, on the side with the associated camera device(s), an overexposure of the image sensors can be prevented, especially after a reducing of the imaging scale, for the same high illumination intensity. It is also possible to employ less light-sensitive sensors and/or color cameras. Preferably, however, at least one adjustable intensity compensation means is provided in which the degree of reduction of the illumination intensity of the camera sensor can be adjusted. A changing of the intensity compensation means in accordance with the set imaging scale of the camera device is also possible. The intensity compensation means is preferably arranged in the illumination direction after the measuring zone and before the objective of the camera device and it constitutes a separate adjustment means for regulating the illumination intensity, separated from the camera.

Since a changing of the magnification or the imaging scale is done according to the invention by adapting or changing the objective of the camera device and not by changing the set level of the illumination intensity, there is no need for a readjustment of the optical system of the illuminating device after changing the imaging scale, which further simplifies the adapting of the magnification to different particle sizes.

According to the invention, each illumination field is assigned at least one separate light source, which simplifies the control of the illumination, especially in the case of pulsed illumination radiation. If the illumination is achieved by means of pulsed illumination radiation, it is preferably provided that the two illumination fields be illuminated in alternation or with a time lag. Thanks to the nonsynchronized light pulses, an overexposure of the image sensors of a camera device can be avoided if the measurement regions intersect or overlap. Depending on the level of the predetermined illumination intensity and/or the arrangement of the measurement regions with respect to each other, both illumination fields can also be illuminated at the same time and/or the light pulses can overlap in time.

The light sources can have matching, especially identical, radiant outputs in Watts per square meter. Preferably, light-emitting diodes (LEDs) of identical design are provided, which can emit for example radiation at the wavelength of 625 nm. In this way, it can easily be assured that both illumination fields can be illuminating with matching intensity.

For the same purpose, lens systems of identical design, each with a plurality of lenses for the imaging of identical illumination beams, can be provided between the light sources and the measuring zone.

In order to make use of the majority of the emitted light and illuminate the illumination fields as homogeneously as possible, in one especially preferred embodiment of the invention identically designed lens systems are arranged between the light sources and the measuring zone, each of them possibly having a plurality of lenses to generate approximately axially parallel beams in relation to the optical axis. In the event that an illumination field is illuminated with a plurality of light sources, a diffuser element can be provided in order to achieve a uniform lighting.

In order to achieve a space-saving structural layout of the illuminating device, two lens systems associated with different light sources can comprise a common lens, especially a meniscus lens, through which the light rays emanating from the light sources pass.

In order to simplify the adjustment of the camera device having the larger imaging scale or photographing a measurement region with a greater magnification, it is advantageous for both illumination fields to have the same size. In any case, the illumination field in which the more strongly magnified measurement region lies is larger than the associated measurement region, so that an easier adjustment of the associated camera device is possible. Thanks to the larger area of the illumination field in which the more strongly magnified measurement region lies, a very homogeneous lighting of this measurement region is ensured.

The illumination beams for the two camera devices can cross in the measuring zone, so that the measurement regions which are photographed by the camera devices are tilted relative to each other. This enables a space-saving arrangement of the optical elements of the illuminating device on the one hand and the camera devices on the other hand and thus a correspondingly small structural size of the device according to the invention. But the camera devices can also be adjusted so that the measurement region which is photographed with a higher magnification lies within the measurement region which is photographed with a lower magnification. The measurement region which is photographed with a higher magnification can also lie entirely outside the measurement region which is photographed with a lower magnification.

The cameras can be designed as digital cameras with a two-dimensional image sensor. The image sensor can be a CCD image sensor or also a CMOS image sensor. The individual light-sensitive elements (pixels) of the image sensor can accept only a limited charge quantity produced by photons. If a pixel is too strongly exposed, this charge quantity will be surpassed and the pixel passes on the surplus charges to the adjacent pixels. Since these also can only receive a limited charge quantity, the result is a formation of bright regions in the photograph, which is undesirable. In order to avoid an overexposure of the image sensor of the camera device during overly high illumination intensity of the measurement region which is being photographed with a lower magnification, and/or when the imaging scale of a camera device is decreased for the same unchanged illumination intensity of the measurement region photographed, the camera device can comprise at least one preferably adjustable intensity compensation means, which is designed and provided to reduce and/or regulate the illumination intensity of the image sensors. The intensity compensation means can be, for example, a diaphragm and/or a neutral density filter. A lower-power objective can also be used as the intensity compensation means. Alternatively, a camera device with less light-sensitive image sensors and/or a camera device with color-sensitive image sensors can be used for the detection of color images, since there is less risk of overexposing the image sensors here. Of course, a combination of several intensity compensation means can also be provided.

Thanks to the use of a camera device comprising low-light image sensors, which are distinguished by less noise, stronger magnifications of a measurement region are possible, even at relatively low illumination intensities of the measurement region.

In order to limit the influence of scattered light, at least one additional diaphragm can be used.

In accordance with the device known from EP 1 972 921 A1, at least one of the camera devices can comprise a telecentric objective, so that the particle size can be determined with adequate precision beyond the focal depth range, within the so-called telecentric range.

The device according to the invention and the method according to the invention are especially suitable for the determination of particle sizes of free-flowing and/or dispersible materials in the range of 0.2 µm to 10 mm, especially 0.7 µm to 3 mm.

The size of the measurement regions or the object fields of the camera devices, the resolutions per pixel and the effective pixel numbers as well as the number of images photographed per second and the measurement limits or dynamic factors may correspond to the values or value ranges mentioned in DE 198 02 141 C1 and/or in EP 1 972 921 A1.

Other features, benefits, and application possibilities of the present invention will emerge from the following description of sample embodiments with the aid of the drawing, and the drawing itself. All described and/or graphically depicted features form the subject matter of the present invention by themselves or in any given combination, regardless of their summarization in the claims or referral back to them.

THE DRAWING SHOWS

Figure 4:
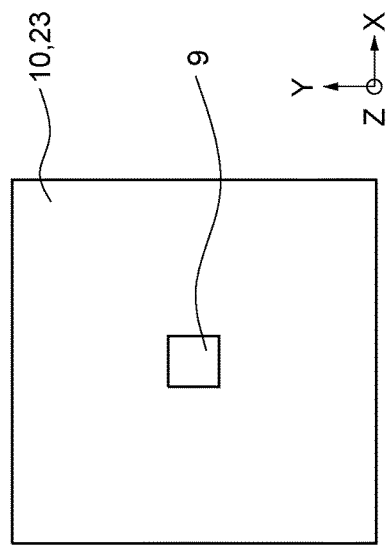
Figure 9:
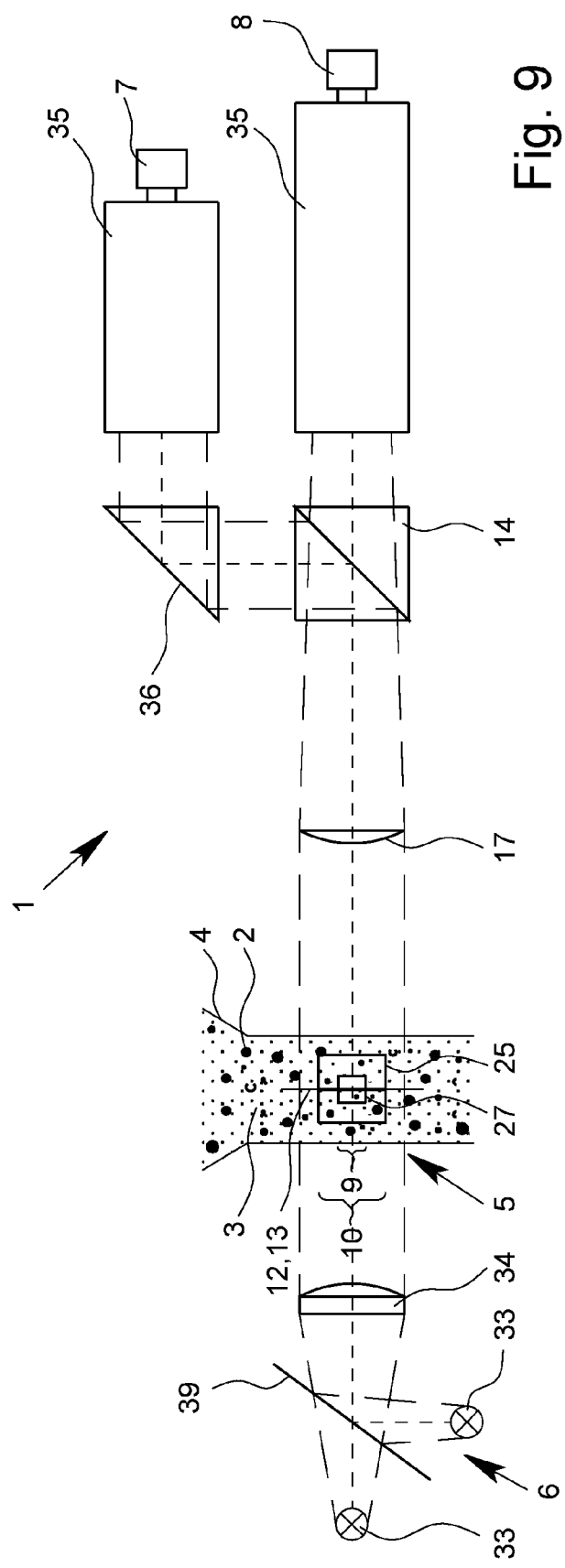
Figure 10:
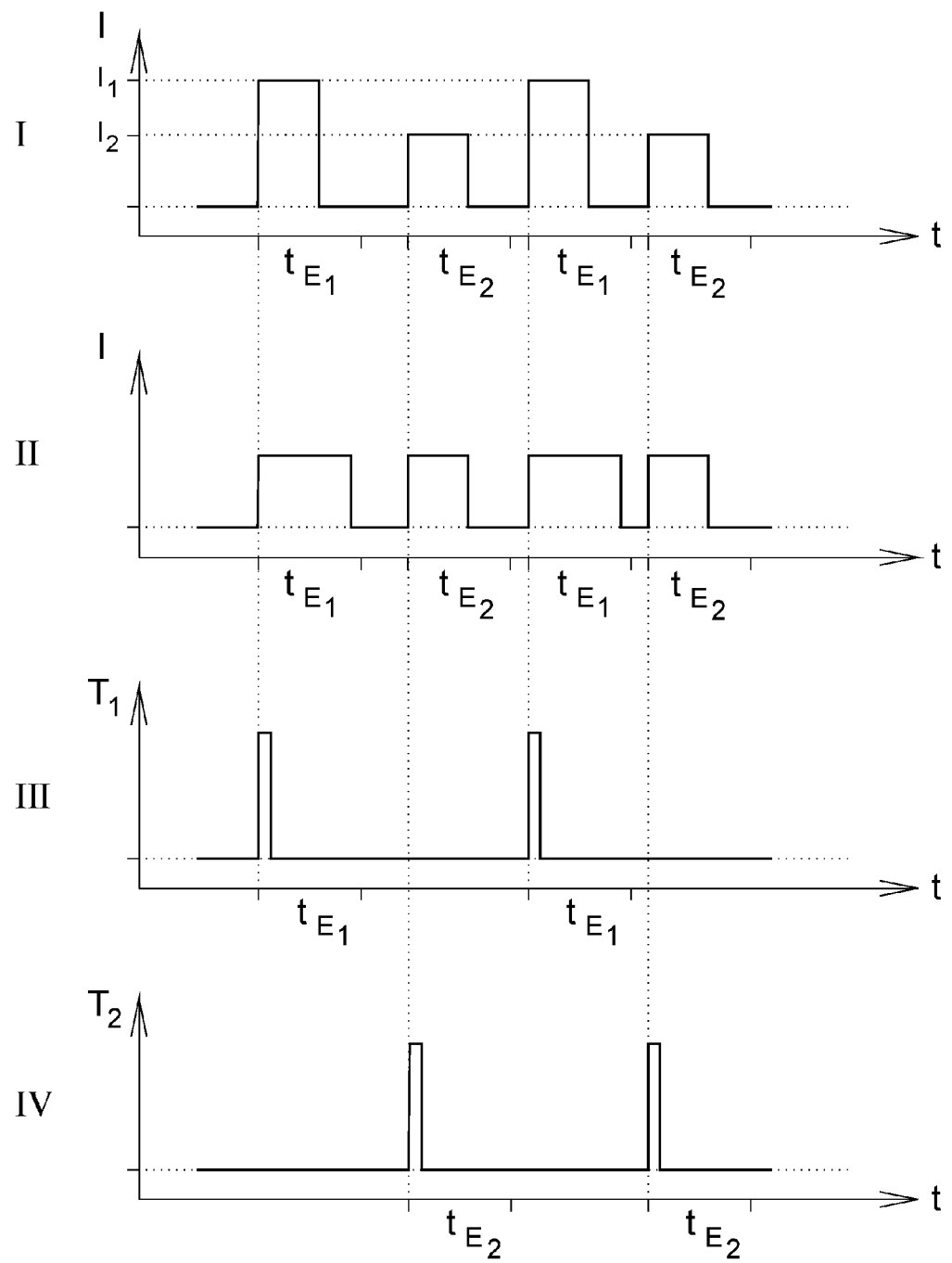
Figure 11:
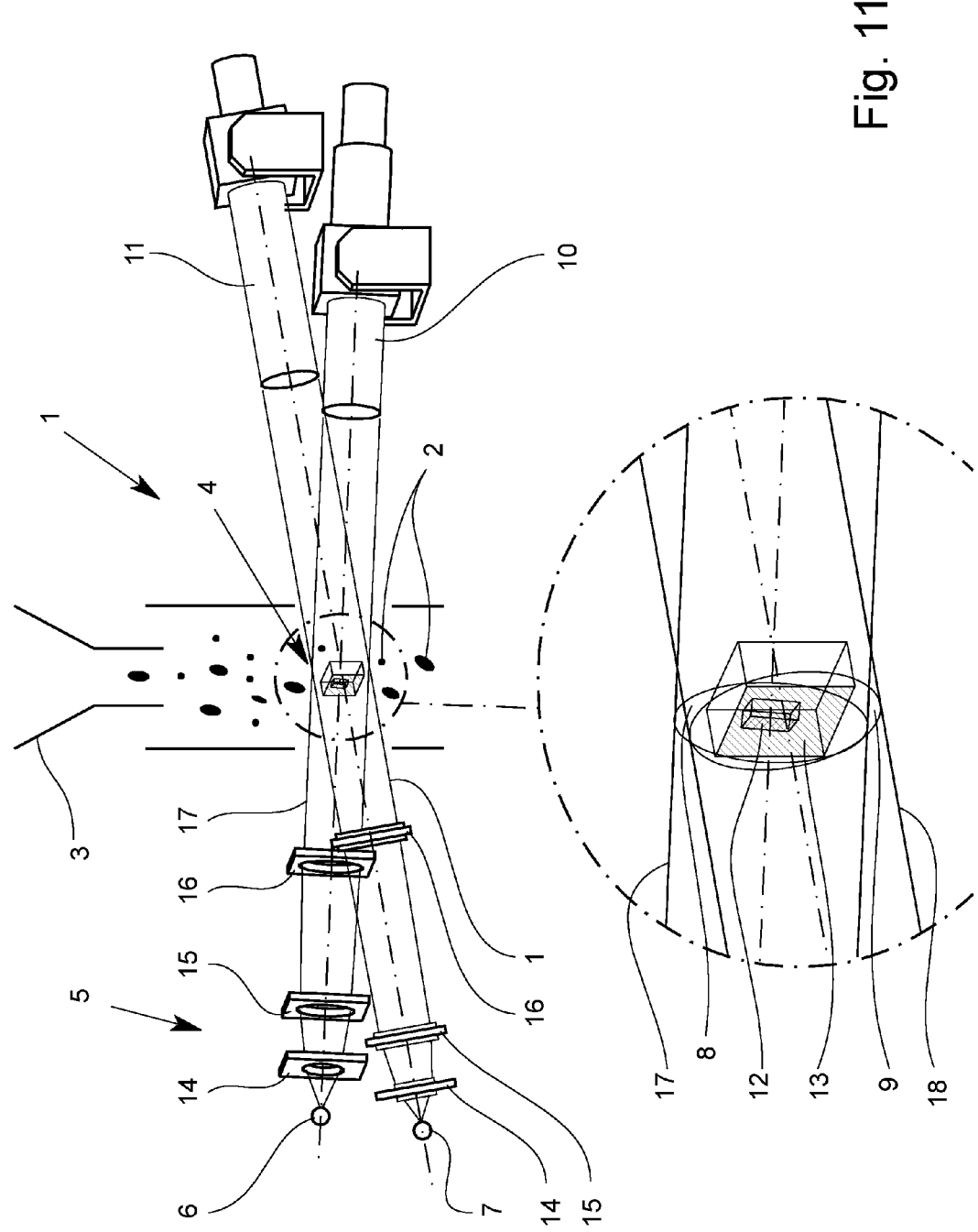

FIG. 1 a schematic representation of a device according to the invention with light rays emanating from a measuring zone of the device, FIG. 2 a schematic representation of the relative position of measurement regions of the measuring zone photographed with two camera devices of the device from FIG. 1, FIG. 3 an alternative embodiment of a device according to the invention, FIG. 4 a schematic representation of the relative position of measurement regions of the measuring zone photographed with three camera devices of the device from FIG. 3, FIG. 5 another alternative embodiment of a device according to the invention, FIG. 6 a schematic representation of the relative position of measurement regions of the measuring zone photographed with four camera devices of the device from FIG. 5, FIG. 7 another alternative embodiment of a device according to the invention, FIG. 8 another alternative embodiment of a device according to the invention, FIG. 9 another alternative embodiment of a device according to the invention, FIG. 10 a schematic representation of the temporal course of the illumination intensity for the illumination of the measuring zone and of control signals for actuating of two camera devices and FIG. 11 a schematic representation of the layout of a device according to the invention for the determination of the particle size(s) and/or the particle shape(s) of particles in a particle stream.

FIGS. 1 to 6 show alternative embodiments of a device 1 for the determination of the particle size and/or the particle shape, and/or optical properties such as transparency, of particles 2 in a particle stream 3, with a feeding device 4 for the feeding of the particles 2 to a measuring zone 5, wherein the particles 2 flow through the measuring zone 5. Furthermore, the device 1 comprises an illuminating device 6 for illuminating the measuring zone 5, at least two camera devices 7, 8, each of them photographing a measurement region 9, 10 of the measuring zone 5 associated with the corresponding camera device 7, 8, an imaging optics 11 for imaging the measurement regions 9, 10, and an evaluating device, not shown, for determining the particle size and/or the particle shape and/or optical properties such as transparency from the photographs of the measurement regions 9, 10. The one camera device 7 for example can photograph the larger measurement region 10 with a lower magnification, while the other camera device 8 photographs the smaller measurement region 9 with a higher magnification.

The illuminating device 6 is designed so that the measurement regions 9, 10 of the measuring zone 5 are always illuminated together, wherein the first measurement region 10 is illuminated with the same intensity as the second measurement region 9. In particular, the illumination intensity undergoes a homogeneous distribution in the entire range of the measurement regions 9, 10. This shall be explained more closely in the further description in connection with FIGS. 7 to 9.

Depending on the position of the camera devices 7, 8 and the layout and arrangement of the optical components of the imaging optics 11, the measurement regions 9, 10 are located in parallel object planes 12, 13. Preferably, the object planes 12, 13 coincide in a common plane. The beams emanating from the measuring zone 5 or the measurement regions 9, 10 travel up to an optical element 14 of the imaging optics 11 for a portion in parallel with an optical axis. This is shown only schematically in FIGS. 1 to 6.

At the optical element 14, the light radiation emanating from the measuring zone 5 is divided into two beam portions, with the intensity of the beam portions not necessarily being identical, and the beam portions in particular can have the identical spectrum. The object planes 12, 13 are projected by the imaging optics 11 into two preferably nonparallel image planes 15, 16. In the image planes 15, 16 are situated the image sensors of the camera devices 7, 8. Between the measuring zone 5 and the optical element 14 on the one hand and the optical element 14 and the respective camera device 7, 8 on the other hand there are provided optical components of the imaging optics 11, in particular lenses 17 and aperture diaphragms 18. The described layout of the device 1 according to the invention enables the determination of the particle size and/or shape with a high precision for a high dynamic measurement region, wherein the adjustment effort during the calibration of the device is slight on account of the measurement regions 9, 10 being arranged in parallel or preferably coinciding object planes 12, 13.

Thanks to additional optical components of the imaging optics 11, for example at least one additional lens and optionally at least one additional aperture diaphragm 20, between the optical element 14 and the camera device 7, different imaging scales result for the photographs of the measurement regions 9, 10 taken by the camera devices 7, 8. For the same size of the image sensors of the camera devices 7, 8, this results in two different-sized measurement regions 9, 10. The smaller measurement region 9, which is photographed with greater magnification, lies as shown in FIG. 2 within the larger measurement region 10, which is photographed with lesser magnification. Preferably, the smaller measurement region 9 lies in the middle of the larger measurement region 10. Alternatively, however, other relative positionings of the measurement regions 9, 10 can also be provided, such as a position of the measurement region 9 in the measurement region 10 at its margin.

The light radiation from the measuring zone 5 impinging on the optical element 14 is divided by the optical element 14 into two beam portions such that the smaller measurement region 9 is illuminated with a higher intensity than the larger measurement region 10. The ratio of the intensity division into the two beam portions is preferably chosen such that the same magnification settings or gain values can be used for both camera devices 7, 8.

In the alternative embodiment of the device 1 according to the invention that is shown in FIG. 3, a further optical element 21 for the dividing of a beam portion generated at the first optical element 14 into two further beam portions and a further camera device 22 are provided. With the three camera devices 7, 8, 22, a total of three measurement regions 9, 10, 23 are photographed. The measurement regions 9, 10, 23 are arranged in three object planes 12, 13, 24, wherein the object planes 12, 13, 24 can be arranged parallel to each other or at least two object planes 12, 13, 24 can coincide.

In the present case, two measurement regions 10, 23 are photographed by the camera devices 7, 22 with the same magnification. These larger measurement regions 10, 23 preferably lie in parallel object planes 13, 24 which are spaced apart in the direction of the optical axis. The smaller measurement region 9 is photographed with a greater magnification and lies in the object plane 12 which coincides with the object plane 13 of the larger measurement region 10. The measurement volumes 25, 26 of the two larger measurement regions 10, 23 pass into one another, so that a broad region results with sufficient image sharpness for the evaluation. In this way, the likelihood of detection of small particles is increased, resulting in a better agreement between the evaluation statistics and the actual particle size distribution. The measurement volume 27 of the smaller measurement region 9 preferably lies within a measurement volume 25, 26 of at least one of the two larger measurement regions 10, 23.

Alternatively, the object planes 13, 24 in which the larger measurement regions 10, 23 lie can also coincide. Thanks to the use of different appropriately designed camera devices 7, 22, a corresponding design of the optical element 21 and/or any other optical components of the imaging optics 11 associated with the camera devices 7, 22, such as filters, in addition to the spatial imaging, it is also possible for example to gain access to spectral or chromatic information.

Of course, alternatively only at least one optical element can be provided in the beam path to the camera device 8 in similar manner to the above, so that the beam portion coming from the first optical element 14 and associated with the camera device 8 is broken up into two beam portions.

In another alternative embodiment of the device 1 according to the invention, represented in FIG. 5, the imaging optics 11 comprises three optical elements 14, 21, 28 as well as four camera devices 7, 8, 22, 29. This results in four measurement regions 9, 10, 23, 30 associated with the camera devices 7, 8, 21, 29. Preferably, two camera devices 8, 29 photograph equal-sized smaller measurement regions 9, 30 with equal greater magnification and the other two camera devices 7, 22 photograph equal-sized larger measurement regions 10, 23 with equal lesser magnification.

In the present case, two measurement regions 10, 23 or 9, 30 photographed with equal magnification by the camera devices 7, 22 or 8, 29 are situated in each instance in object planes 12, 13, 24, 31, while the object planes 13, 24 in which the larger measurement regions 10, 23 lie and the object planes 12, 31 in which the smaller measurement regions 9, 30 lie are spaced apart from each other in the direction of the optical axis. The measurement volumes 25, 26 of the two larger measurement regions 10, 23 pass into one another. The same holds for the measurement volumes 27, 32 of the two smaller measurement regions 9, 30. In this way, broad continuous regions are produced with sufficient image sharpness for the evaluation for both pairs of measurement regions. In turn, the detection probability for small particles can be increased in this way and at the same time a large dynamic measurement region can be achieved. The measurement volumes 27, 32 of the smaller measurement regions 9, 30 preferably lie within the measurement volumes 25, 26 of the two larger measurement regions 10, 23.

It is furthermore possible for two measurement regions 9, 30 or 10, 23 that are photographed with the same magnification to lie in object planes 12, 31 or 13, 24 which coincide in each instance. In this way, once again an access to spectral or chromatic information is enabled, for example, in addition to the spatial imaging.

Preferably, the object planes 13, 24 of the larger measurement regions 10, 23 and the object planes 12, 31 of the smaller measurement regions 9, 30 coincide in each instance. As a result, the object planes 12, 13, 24, 31 of all measurement regions 9, 10, 23, 30 thus lie in a common plane.

Given matching measurement volumes 27, 32 or 25, 26 of the measurement regions 9, 30 or 10, 23 photographed in each instance with the same magnification, and thanks to the use of different appropriately designed camera devices 8, 29 or 7, 22, an appropriate design of the optical elements 21, 28 and/or any other optical components of the imaging optics 11 associated with the camera devices 8, 29 or 7, 22, such as filters, it is possible to obtain spectral or chromatic information in addition to the spatial imaging, while at the same time assuring a large dynamic measurement region.

In the embodiment of the device according to the invention shown in FIG. 7, an illuminating device 6 with a nearly pointlike radiation source 33 is provided, which at first emits light isotropically, i.e., equally in all spatial directions. A portion of the light given off by the radiation source 33 is made parallel by a collimator lens 34. This produces a homogeneous illumination of the sample in the region of the measuring zone 5 with a substantially parallel radiation path.

The measurement regions 9, 10 are always illuminated together, with the first measurement region 9 being lit with the same intensity as the second measurement region 10. The radiation source 33 is an LED in particular, preferably a high-power LED.

The radiation source 33 can substantially emit light in any wavelength range which can be detected by the camera devices 7, 8. Thus, it is possible either to use a white-light LED with a relatively broad emission spectrum and an LED which emits light of a particular color, i.e., in a limited wavelength range. Furthermore, it is possible to use a multicolor emitting LED, especially a RGB LED, so that the color of the light given off is selectable or adjustable.

The light traveling from the measuring zone 5 in the direction of the camera devices 7, 8 passes through an optional lens 17 between the measuring zone 5 and the optical element 14 in the sample embodiment shown in FIG. 7. The lens 17 constitutes a common optical element of the imaging optics 11 for both observation channels. That is, in this case the lens 17 is associated with both camera devices 7, 8. Depending on the design of the lens 17, the imaging can be influenced in a desired way.

Besides a general focusing or defocusing property, preferably with relatively large focal width, the lens 17 can be designed in particular for correction of imaging errors.

After moving through the optical element 14, the light from the measuring zone 5 arrives at the camera devices 7, 8, each with their own upstream imaging optics, which in the present representation is accommodated inside a tube 35 and not shown in detail.

In the case of the first camera device 7, the light also passes through a deflection mirror 36, so that the two camera devices 7, 8 along with the tubes 35 with the imaging optics inside them can be arranged parallel to each other or alongside each other. This achieves a compact layout of the device according to the invention.

Preferably, the illuminating device 6 has a pulsed operation, so that a stroboscopic illumination of the measuring zone results. By alternating illumination of the measuring zone with pulses of higher intensity and pulses of lower intensity, or pulses of longer and shorter duration, the measuring zone 5 can be illuminated with varying strength, while at the same time the measurement regions 9, 10 are always illuminated together and at the same time with the same intensity.

Thanks to an appropriate control, especially a synchronization, of the camera devices 7, 8 with the illuminated device 6, each of the camera devices 7, 8 is exposed with sufficient strength in accordance with its magnification. In this case, the optical element 14 can bring about a division of the incident light radiation into beam portions of equal intensity, i.e., in a ratio of 50:50.

In the case of a comparative investigation of particles occurring both in the picture of the first camera device 7 and in the picture of the second camera device 8, the illuminating device 6 can also emit pulses of equal length and intensity, by means of which the measurement regions 9, 10 are illuminated together and with the same intensity. In this way, the spatial position of the particles detected with the second camera device 8 in the larger measurement region 10 photographed by the first camera device 7 can be assured. For an adequate exposure of the chip of the second camera device 8, the incident light radiation can be divided into two beam portions of different intensity at the optical element 14. In this way, the second camera device 8 which photographs the second, smaller measurement region 9 with greater magnification can be assigned a larger share of the overall intensity, so that the exposure is strong enough for an evaluation of the image.

The sample embodiment of the device according to the invention that is shown in FIG. 8 corresponds in its layout substantially to the embodiment represented in FIG. 7. The differences concern the illuminating device 6, which in FIG. 8 is designed as an area light source 37. The area light source 37 in the present form comprises a plurality of individual radiation sources 33 on the inside. By a scattering disk 38, which covers the radiation sources 33 on the side of the area light source 37 facing the measuring zone 5 and generally consists of or comprises a translucent but nontransparent material, which means that it is not possible to see through the material.

While the light radiation emitted by the radiation sources 33 can pass through the scattering disk 38, its direction of propagation is randomly altered by scattering, so that an emission of light occurs in a nondirected and preferably homogenous manner over the entire surface of the scattering disk 38. Thanks to the use of such an area light source 37 of sufficient size, the image background as seen from the direction of observation of the camera devices 7, 8 can be illuminated uniformly, so that particles being detected can be observed with high contrast and sharp contours in the region of the measuring zone 5.

Alternatively to an area light source 37 with the above-described composition, an electroluminescent film can also be used alternatively for the same purpose.

Just like the illuminating device 6 in the sample embodiment shown in FIG. 7, the area light source 37 represented in FIG. 8 can also have a pulsed operation. The statements regarding different pulse intensities and/or durations hold as well in this case.

The sample embodiment shown in FIG. 9 corresponds in its composition to the sample embodiments per FIGS. 7 and 8 downstream of the measuring zone 5. The illuminating device 6 in the present case comprises two individual, nearly pointlike radiation sources 33. The light emitted by the radiation sources 33 is in part combined by a semitransparent minor 39 and made parallel by a collimator lens 34, so that in its further path the beam geometry corresponds to the sample embodiment per FIG. 7. Thanks to the use of two individual radiation sources 33, for example, it is possible to simplify the actuating of the illuminating device 6 for a stroboscopic illumination with alternating pulses of different intensity and/or duration.

For example, two radiation sources 33 with the same emission spectrum, but different power, can be actuated in alternation by a relatively simple trigger electronics, so that a joint illumination of the measurement regions 9, 10 results with the same intensity for the measurement regions 9, 10, yet with alternating intensity over time.

The optical element 14 in this case, similar to the sample embodiment per FIG. 7, divides the incident light radiation coming from the measuring zone 5 into two beam portions of the same intensity. By a synchronization of each of the camera devices 7, 8 to one radiation source 33 of the illuminating device 6 by means of the trigger electronics, it is guaranteed that the taking of a picture always occurs under an illumination of the measurement regions 9, 10 with a quantity of light adapted in each case to the optical and electronic photography parameters of the camera device 7, 8.

The use of two radiation sources 33 furthermore also enables an illumination of the measurement regions 9, 10 with light of different wavelength. For this, the radiation sources 33 of the illuminating device 6 can have different emission spectra. The optical element 14 in this case divides the incident, polychromatic light radiation depending on wavelength into at least two beam portions. These beam portions can substantially have the same or different intensities.

The two radiation sources 33 of the illuminating device 6 can on the one hand be actuated in alternation in the manner described in order to illuminate the measuring zone 5 in alternation in pulsed fashion with light of the different radiation sources 33. Alternatively, of course, the radiation sources 33 can also be actuated jointly and thus jointly illuminate the measurement regions 9, 10. The intensities of the light radiation given off by the radiation sources 33 add up in this case to an overall intensity with which the measurement regions 9, 10 are jointly illuminated.

The synchronization of the camera devices 7, 8 with the illuminating device 6 can be understood with reference to signals I to IV represented in the joint time curve of FIG. 10.

In the case of the intensity I emitted by the illuminating device 6, one can see per diagram I of the time curve an alternating sequence of light pulses of the same length, but with different intensity. In comparison, diagrams III and IV show the trigger signals for actuating the different camera devices 7, 8 in a time curve.

By the actuating of the camera device 8, which photographs the smaller measurement region 9 with a greater magnification, with the trigger signal $T_1$ per the representation in diagram III, the taking of a picture with a certain exposure time $t_{E1}$ is triggered synchronously for each light pulse with a higher intensity $I_1$. By the actuating of the camera device 7, which photographs the larger measurement region 10 with lesser magnification, with a trigger signal $T_2$ having a time curve per diagram IV, a picture is taken each time with an exposure time $t_{E2}$ by means of the camera device 7. In turn, this photographing is synchronous to the light pulses with a lesser intensity $I_2$ per diagram I.

Alternatively, the pulsed illumination of the measuring zone 5 can also be realized with light pulses of the same intensity, but different length. A sample curve of the light intensity I emitted by the illuminating device 6 is shown in the joint time curve with diagrams I, III and IV in diagram II.

By the actuating of the camera device 8, which photographs the smaller measurement region 9 with a greater magnification, in accordance with the time signal curve per diagram III, the taking of a picture is triggered synchronously to the light pulses of longer duration each time. In corresponding manner, the taking of a picture with the camera device 7, which [photographs] the larger measurement region 10 with lesser magnification, by the trigger signal $T_2$ represented in diagram IV, is done synchronously to the shorter-time pulses per diagram II.

Despite the equal maximum intensity of the light pulses represented in diagram II, during the exposure time $t_{E1}$ more light gets onto the chip of the camera device 8 synchronized with the longer pulses than arrives during the exposure time $t_{E2}$ at the chip of the camera device 7 synchronized with the shorter pulses. Since the camera devices 7, 8 integrate the light intensity impinging on the sensor chip over the entire exposure time $t_E$, it is ultimately a question of the area during a light pulse to which the chip of the corresponding camera device 7, 8 is exposed. A brighter image therefore results during both a higher and a longer pulse. The exposure time $t_E$ in the camera devices customarily used is significantly greater than the maximum effective illumination duration during stroboscopic illumination of rapidly moved objects, such as particles 2 in a particle stream 3.

In FIG. 11 a device 1 is shown for the determination of the particle size and/or the particle shape of particles 2 in a particle stream, the particles 2 being fed with a feeding device 3 to a measuring zone 4. After this, the particles 2 flow through the measuring zone 4. The feeding device 3 is shown only schematically and may have a funnel, to which a feed trough is attached. The feeding device 3 can rest on a lower structure, having an adjustment device with which the feed trough can be oriented in particular in the horizontal, transversely to the particle stream dropping onto the feed trough. Beneath the lower structure, a catching receptacle can be arranged to catch the particle stream.

The measuring zone 4 is transparent to the illumination radiation, which shall be described more closely below. The illumination of the measuring zone 4 is done with an illuminating device 5 comprising two light sources 6, 7, emitting coinciding radiant powers. The first light source 6 illuminates a first illumination field 8 of the measuring zone 4, while the second light source 7 illuminates or lights up a second illumination field 9 of the measuring zone 4. The illumination fields 8, 9 are only shown schematically.

Furthermore, two camera devices 10, 11 are provided in order to photograph two measurement regions 12, 13 or image-detecting surfaces of the measuring zone 4 digitally in the form of pixels covered by the projection surfaces of the particles in the respective camera device. The measurement regions 12, 13 lie in the planes of the illumination fields 8, 9.

An evaluating device not shown in the figure serves for the determining of the particle sizes and/or the particle shapes from the photographs of the measurement regions 12, 13, which is known to the skilled person from the prior art, especially DE 198 02 141 C1 and/or EP 1 972 921 A1.

In the device 1, two camera devices 10, 11 are provided in order to increase the dynamic range of the measurement, i.e., the region of measurable particle sizes. The one camera device 10 photographs a first, preferably smaller, measurement region 12 with a greater magnification, while the other camera device 11 photographs another, preferably larger, measurement region 13 with a lesser magnification. The camera devices 10 are shown schematically and comprise different objectives.

As is further seen from the figure, the more magnified measurement region 12 lies in the first illumination field 8, while the less magnified measurement region 13 lies in the second illumination field 9. For example, the camera device 10 can photograph the more magnified measurement region 12 with 8× magnification, while the camera device 11 photographs the less magnified measurement region 13 with 2× magnification.

In order to enable a simple, especially a customer-specific adapting of the imaging scale during the photographing of at least one measurement region 12, 13, especially during the photographing of the measurement region 12 with the higher magnification, to different particle sizes of the particles 2, the illumination of the two illumination fields 8, 9 is done with matching, preferably identical, intensity. In this case, the intensity of the illumination of the two illumination fields 8, 9 is set at a particular magnification of the more magnified measurement region 12 and can be kept the same upon changing the imaging scale of a camera device 10, 11 or even the imaging scales of both camera devices 10, 11. In other words, each illumination field is illuminated with a matching intensity, needed to accomplish sharp and contrast-rich photographs of the particles 2 in a measurement region 12, 13 at a given magnification, such as 4×, 8×, 10×, 12× or 20×, by the respective camera device 10, 11. The level of the illumination intensity is adapted to a given imaging scale of one of the two camera devices 10, 11. In particular, it is not provided to set for each measurement region 12, 13 an optimal intensity in accordance with the magnification by the respective camera device 10, 11 and/or aperture of the objective of the respective camera device 10, 11.

As further emerges from the figure, identically designed lens systems with a plurality of lenses 14-16 are provided between the light sources 6, 7 and the measuring zone 4 in order to generate approximately axially parallel beams 17, 18. In this way, identical illumination beam paths are realized between the light sources 6, 7 and the measuring zone 4, in order to assure a matching illumination intensity for the illumination of the illumination fields 8, 9.

The light sources 6, 7 may consist of one or more light-emitting diodes. In the event that several LEDs are used, a diffuser element can be provided in addition. The first lens 14 of the lens system can be a concavoconvex lens with a focal distance of f=+50 mm, for example. The second lens 15 and the third lens 16 can be designed as planoconvex lenses with a focal distance of f=+50 mm and f=+100 mm, for example. The spacing between the pointlike light sources 6, 7 and the first lens 14 is relatively short and can amount to less than 20 mm, for example 7 to 8 mm. Since the LEDs which are used have large emission angles, most of the emitted light can be utilized with the described lens system to illuminate the illumination fields 8, 9. After the third lens 16, the beams 17, 18 are oriented approximately axially parallel to the optical axis and an illumination field 8, 9 with a diameter of 30 mm, for example, can be homogeneously illuminated each time. The size of the illumination fields 8, 9 simplifies the adjustment of the camera devices 10, 11, which is especially true for the camera device 10, which photographs the smaller measurement region 12 with a larger imaging scale. The size of the measurement regions 12, 13 or the size of the image detection surfaces and/or the size of the cross sectional areas of the illumination fields 8, 9 can differ from the sizes depicted. Of course, the aforementioned lens shapes and focal distances of the lenses 14 to 16 are merely a preferred embodiment.

By the way, it is not shown that at least one common lens through which the two illumination beams pass can be provided between the light sources 6, 7 and the measuring zone 4 in order to reduce the space requirement. For example, it is possible to provide a larger common meniscus lens in place of the two third and last lenses of the two lens systems.

Neither is it shown, moreover, that at least one camera device 10, 11 can have an intensity compensation means, such as a diaphragm, a filter or an objective with less light sensitivity, in order to prevent an overexposing of the camera sensor on account of too high a setting of the illumination intensity. This applies in particular to the camera device 11, which photographs the measurement region 13 with lesser magnification. Basically, however, an intensity compensation means can also be provided in the camera device 10 if its imaging scale is reduced in order to adapt to a particular particle size and the illumination intensity setting is kept unchanged.

| List of reference numbers: | |
|---|---|
| 1 | Device |
| 2 | Particle |
| 3 | Particle stream |
| 4 | Feeding device |
| 5 | Measuring zone |
| 6 | Illuminating device |
| 7 | Camera device |
| 8 | Camera device |
| 9 | Measurement region |
| 10 | Measurement region |
| 11 | Imaging optics |
| 12 | Object plane |
| 13 | Object plane |
| 14 | Optical element |
| 15 | Image plane |
| 16 | Image plane |
| 17 | Lens |
| 18 | Aperture diaphragm |
| 19 | Lens |
| 20 | Aperture diaphragm |
| 21 | Optical element |
| 22 | Camera device |
| 23 | Measurement region |
| 24 | Object plane |
| 25 | Measurement volume |
| 26 | Measurement volume |
| 27 | Measurement volume |
| 28 | Optical element |
| 29 | Camera device |
| 30 | Measurement region |
| 31 | Object plane |
| 32 | Measurement volume |
| 33 | Radiation source |
| 34 | Collimator lens |
| 35 | Tube |
| 36 | Deflection mirror |
| 37 | Area light source |
| 38 | Scattering disk |
| 39 | Semitransparent mirror |

The invention claimed is:

1. Device for determination of particle size, particle shape, or optical properties of particles in a particle stream, with a feeding device for the feeding of the particles to a measuring zone, wherein the particles flow through the measuring zone, with an illuminating device for irradiating through the measuring zone, with at least two camera devices, each of which photographs a measurement region of the measuring zone associated with the corresponding camera device, wherein a first camera device photographs a first larger measurement region with a first lesser magnification and a second camera device photographs a second smaller measurement region with a second greater magnification, with an imaging optics for imaging the measurement regions and with an evaluating device for determining particle size or particle shape from the photographs of the two measurement regions, wherein the imaging optics comprises an optical element arranged between the measuring zone and the first and second camera devices, wherein the light radiation emanating from the measuring zone in a common optical path before the optical element is divided into at least two beam portions after the optical element associated with the first and second camera devices, wherein the illuminating device and the measuring zone are positioned in the common optical path before the optical element and the first and second camera devices are positioned in the at least two beam portions after the optical element, wherein the first and second camera devices photograph the measuring zone at the same angle and, wherein the measurement regions are situated in at least one object plane and the at least one object plane is projected by the imaging optics into at least two image planes, in which image sensors of the first and second camera devices are located,
wherein the illuminating device is designed such that the first measurement region and the second measurement region are always illuminated together, wherein the first measurement region is illuminated with the same intensity as the second measurement region.

2. Device according to claim 1, wherein the optical element divides the incident light radiation coming from the measuring zone into the at least two beam portions, which are identical in spectrum to the incident light radiation.

3. Device according to claim 1, wherein the illuminating device comprises at least two light sources emitting light radiation of a least one of a different wavelength and a different wavelength region, wherein the optical element divides the incident light radiation coming from the measuring zone into the at least two beam portions depending on wavelength.

4. Device according to claim 1, wherein the illuminating device is designed for the joint homogeneous illumination of the two measurement regions.

5. Device according to claim 1, wherein the measurement regions are exposed in sequence, in alternation, with light radiation of different intensity.

6. Device according to claim 1, wherein the illuminating device is designed for pulsed illumination of the two measurement regions, wherein at least one of duration and intensity of at least two pulses is different, wherein a first pulse with at least one of lower intensity and shorter duration illuminates the two measurement regions, while the first camera device photographs the first larger measurement region with a first lesser magnification, and a second pulse with at least one of higher intensity and longer duration illuminates the two measurement regions while the second camera device photographs the second smaller measurement region with a second greater magnification and wherein at least one first and second camera devices is synchronized with the illuminating device.

7. Device according to claim 1, wherein the imaging optics comprises at least one of a lens arranged between the measuring zone and the optical element and at least one lens with a variable, electrically changeable focal distance.

8. Device according to claim 1, wherein the measurement regions are situated in parallel or coinciding object planes.

9. Device according to claim 1, wherein spacing of two object planes from each other can be adjusted so that one measurement volume associated with a more magnified measurement region lies entirely in a measurement volume associated with a less magnified measurement region.

10. Device according to claim 1, wherein the optical element is designed so that the at least two beam portions have different light intensities.

11. Device according to claim 1, wherein at least three camera devices are provided and the imaging optics comprises at least one additional optical element, at which a beam portion is divided into two further beam portions.

12. Device according to claim 1, wherein spacing of the object planes of at least two measurement regions from each other can be adjusted so that one measurement volume of one measurement region and one measurement volume of another equally-sized measurement region pass into each other.

13. Device according to claim 1, wherein the imaging optics comprise at least two optical elements, wherein one optical element divides light radiation into at least two beam portions with at least one of identical spectrum, identical color, and identical polarization and another optical element divides light radiation into at least two beam portions with at least one of different spectra, different colors, and different polarizations.

14. Device according to claim 1, wherein the imaging optics is designed so that the first and second camera devices are provided to photograph an identical measurement volume, having different detection properties that depend on wavelength.

15. Method for determination of particle size, particle shape, or optical properties of particles in a particle stream, wherein the particles flow through a measuring zone, wherein the measuring zone is irradiated by at least one illuminating device, wherein at least two camera devices each photograph a measurement region of the measuring zone associated with the corresponding camera device wherein a first camera device photographs a first larger measurement region with a first lesser magnification and a second camera device photographs a second smaller measurement region with a second greater magnification, wherein the measurement regions are imaged by an imaging optics, wherein particle size or particle shape is determined from the photographs of the two measurement regions for a high dynamic measurement region by an evaluation device, wherein the light radiation emanating from the measuring zone in a common optical path is divided by at least one optical element of the imaging optics arranged between the measuring zone and the first and second camera devices into at least two beam portions associated with the first and second camera devices, wherein the at least one illuminating device and the measuring zone are positioned in the common optical path before the at least one optical element and the first and second camera devices are positioned in the at least two beam portions after the at least one optical element, wherein the first and second camera devices photograph the measuring zone at the same angle, and wherein the measurement regions are situated in at least one object plane and the at least one object is projected by the imaging optics into at least two image planes, in which image sensors of the first and second camera devices are located, wherein the first measurement region and the second measurement region are always illuminated together, wherein the first measurement region is illuminated with the same intensity as the second measurement region.

* * * * *